(12) United States Patent
Gruber et al.

(10) Patent No.: US 6,308,358 B2
(45) Date of Patent: *Oct. 30, 2001

(54) TOOTHBRUSH COMPRISING A BRUSH MEMBER HAVING A BRISTLE FIELD AND AN INTERDENTAL BRISTLE FIELD

(75) Inventors: Paul Gruber, Klagenfurt (AT); Stein Edvardsen, Skedsmokorset (NO)

(73) Assignee: U.S. Philips Corporation, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,319

(22) Filed: Apr. 30, 1999

(30) Foreign Application Priority Data

May 5, 1998 (EP) .................................................. 98890126

(51) Int. Cl.⁷ ..................................................... A46B 13/02
(52) U.S. Cl. ............................ 15/22.1; 15/28; 15/DIG. 5
(58) Field of Search ................................. 15/22.1, 22.2, 15/28, DIG. 5

(56) References Cited

U.S. PATENT DOCUMENTS 3,177,509 * 4/1965 Cyzer ........................................ 15/28

FOREIGN PATENT DOCUMENTS

| 4309035A1 | 9/1994 | (DE) . |
| 97/01357 | 1/1997 | (WO) . |
| 97/24079 | 7/1997 | (WO) . |

* cited by examiner

Primary Examiner—Randall E. Chin
(74) Attorney, Agent, or Firm—Ernestine C. Bartlett

(57) ABSTRACT

In a toothbrush having a brush member which carries a bristle holder with a bristle field and an interdental bristle holder with an interdental bristle field, the bristle field comprises a first field portion and a second field portion, the first field portion being disposed nearer the interdental bristle field than the second field portion and the bristles of the first field portion being shorter than the interdental bristles and the bristles of the second field portion being longer than the bristles of the first field portion and thus at the same time form interdental bristles.

6 Claims, 2 Drawing Sheets

TOOTHBRUSH COMPRISING A BRUSH MEMBER HAVING A BRISTLE FIELD AND AN INTERDENTAL BRISTLE FIELD

BACKGROUND OF THE INVENTION

The invention relates to a toothbrush comprising a grip member and a brush member connected to the grip member, which brush member has a longitudinal axis and at its end remote from the grip member carries a bristle holder which is reciprocatingly drivable through a center position, which bristle holder is mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, which bristles together form a bristle field, and which in addition comprises an interdental bristle holder, which is reciprocatingly drivable through a center position and is disposed adjacent the bristle holder in the direction of the longitudinal axis of the brush member, which interdental bristle holder is mounted on the brush member so as to be movable and has a further holder surface and from which in the area of the further holder surface interdental bristles project transversely to the further holder surface, which interdental bristles together form an interdental bristle field.

The invention further relates to a brush member for a toothbrush which brush member is adapted to be coupled detachably to a grip member of the toothbrush and which brush member has a longitudinal axis and at its end remote from the grip member carries a bristle holder which is reciprocatingly drivable through a center position, which bristle holder is mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, which bristles together form a bristle field, and which in addition comprises an interdental bristle holder, which is reciprocatingly drivable through a center position and is disposed adjacent the bristle holder in the direction of the longitudinal axis of the brush member, which interdental bristle holder is mounted on the brush member so as to be movable and has a further holder surface and from which in the area of the further holder surface interdental bristles project transversely to the further holder surface, which interdental bristles together form an interdental bristle field.

Such a toothbrush of the type defined in the first paragraph and such a brush member of the type defined in the second paragraph are known, for example from the patent document WO 97/24079. The bristles of the bristle field of this known toothbrush and this known brush member have bristle lengths within a given nominal range, all the bristles on the bristle holder having a smaller length than the interdental bristles, i.e. being smaller than the interdental bristles. As a result of this configuration the situation is obtained that with the known toothbrush and the known brush member the bristles of the bristle holder serve mainly for cleaning the teeth at the location of their easily accessible lateral surfaces and, if desired, their masticatory surfaces and the interdental bristles mainly serve for cleaning the teeth at the location of the interdental spaces. In practice, it has been found that, although a satisfactory cleaning performance can be obtained with the known toothbrush, the attainable cleaning performance is still open to improvement. It is to be noted that in the patent document WO 97/24079 A1the patent document DE 43 09 035 A1is mentioned, which is incorporated herewith by reference.

SUMMARY OF THE INVENTION

It is an object of the invention to improve a toothbrush of the type defined in the first paragraph and a brush member of the type defined in the second paragraph in a simple manner and by simple means in order to obtain an improved toothbrush and an improved brush member.

According to the invention, in order to achieve this object a toothbrush of the type defined in the first paragraph is provided in which the bristle field comprises a first field portion and a second field portion, the first field portion is disposed at the side of the bristle holder nearest the interdental bristle field and the second field portion is disposed at the side of the bristle holder remote from the interdental bristle field, the bristles of the first field portion are shorter than the interdental bristles, the bristles of the second field portion are longer than the bristles of the first field portion and the bristles of the second field portion thus at the same time form interdental bristles. In accordance with the invention an improved toothbrush is obtained in a very simple manner and by simple means, which hardly require any additional expense. In a toothbrush in accordance with the invention, some of the bristles on the bristle holder are also available for the purpose of cleaning teeth in the interdental spaces. In addition to a distinctly improved removal of plaque in the interdental spaces by means of the bristles in the second field area of the bristle field, these bristles already present in the second field in conjunction with the interdental bristles provide a satisfactory positioning of the whole bristle configuration of the brush member with respect to a tooth to be cleaned, which is advantageous for a proper cleaning of the teeth at the location of their lateral surfaces.

In a toothbrush in accordance with the invention it has proved to be advantageous in preferred embodiments of the invention to provide such a toothbrush wherein all the bristles of the first field portion have the same length and wherein the bristles of the second field portion are bounded at their free ends by two bounding planes which are inclined with respect to one another in a wedge-like fashion.

According to the invention, in order to achieve the object mentioned hereinbefore, a brush member of the type defined in the second paragraph is characterized in that the bristle field comprises a first field portion and a second field portion, the first field portion is disposed at the side of the bristle holder nearest the interdental bristle field and the second field portion is disposed at the side of the bristle holder remote from the interdental bristle field, the bristles of the first field portion are shorter than the interdental bristles, the bristles of the second field portion are longer than the bristles of the first field portion and the bristles of the second field portion thus at the same time form interdental bristles. This provides a brush member in accordance with the invention by means of which the advantages expounded hereinbefore for a toothbrush in accordance with the invention can be obtained.

The above-mentioned as well as further aspects of the invention will become apparent from the embodiment described hereinafter by way of example and will be elucidated on the basis of this embodiment.

BRIEF DESCRIPTION OF THE DRAWINGS

The invention will now be described in more detail with reference to the drawings, which show an embodiment, given by way of example, to which the invention is not limited.

DESCRIPTION OF THE PREFERRED EMBODIMENTS

Figure 1:
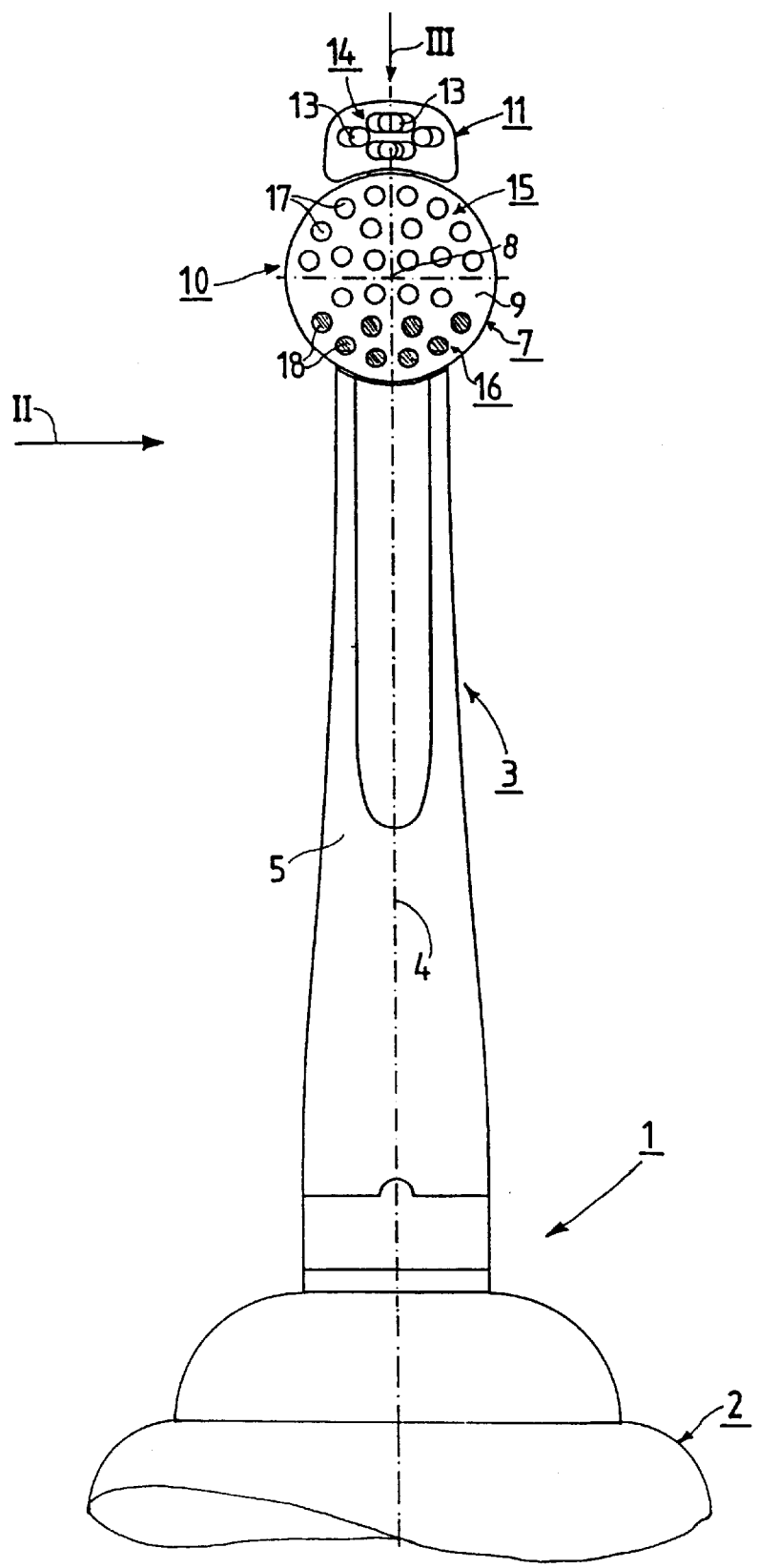
FIG. 1 is a plan view to twice the full-size scale showing the relevant part of a toothbrush in accordance with an embodiment of the invention, which part of the toothbrush includes the brush member of this toothbrush.

FIG. 1 shows the relevant parts of a toothbrush 1 in accordance with the invention. The toothbrush 1 has a grip member 2, which is shown only partly in FIG. 1, and a brush member 3 connected to the grip member 2. As regards a possible construction of the grip member 2 and the drive means for driving the bristles of the brush member, which means are accommodated in the grip member 2 and partly in the brush member 3, reference is made to the document WO 97/24079 A1 mentioned in the introductory part and to the international patent application bearing the application number PCT/IB 97/01357, which is incorporated herewith by reference.

The brush member 3 comprises a tubular portion 5, which extends in the direction of a longitudinal axis 4 of the brush member 3, and a disc portion 6 which is integrally connected to the tubular portion 5 at that end of the tubular portion 5 which is remote from the grip member 2.

Figure 2:
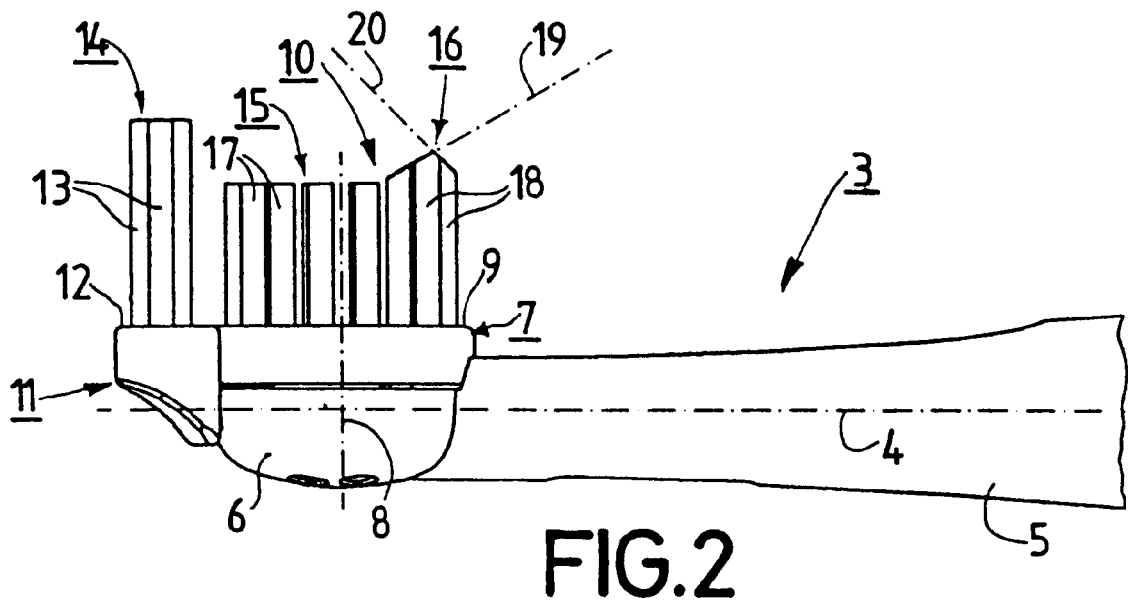
FIG. 2 shows the brush member of the toothbrush of FIG. 1 in a side view to the same scale as in FIG. 1 and taken at the arrow II in FIG. 1.
Figure 3:
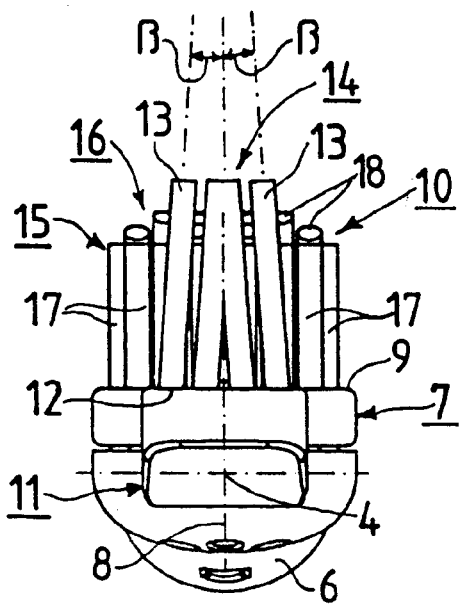
FIG. 3 shows the brush member of the toothbrush of FIGS. 1 and 2 in a front view to the same scale as in FIGS. 1 and 2 and taken at the arrow III in FIG. 1.

The disc portion 6 and, consequently, the end of the brush member 3 remote from the grip member 2 carries a bristle holder 7, which is driveable for pivotable movement between multiple positions through a center position shown in FIGS. 1, 2 and 3. The bristle holder 7 is mounted on the brush member 3, namely on the disc portion 6 of the brush member, so as to be movable, i.e. pivotable, with respect to a holder axis 8 which extends transversely to the longitudinal axis 4, in the present case exactly perpendicularly to the longitudinal axis 4. The bristle holder 7 is drivable by drive means, not shown, and performs pivotal movement along a circular path when it is driven.

The bristle holder 7 has a holder surface 9 which extends transversely to the holder axis 8, in the present case perpendicularly to the holder axis 8. Bristles project from the bristle holder 7 in the area of the holder surface 9 and extend transversely to the holder surface 9, in the present case perpendicularly to the holder surface 9. The bristles which project from the bristle holder 7 together form a bristle field 10.

Moreover, the brush member 3 has an interdental bristle holder 11 which is driveable for pivotable movement between multiple positions through a center position also shown in FIGS. 1, 2 and 3 and which is disposed adjacent the bristle holder 7 in the direction of the longitudinal axis 4. In the toothbrush 1 shown in FIGS. 1, 2 and 3 the interdental bristle holder 11 is disposed adjacent the bristle holder 7 at the side of this holder 7 which is remote from the grip member 2. The interdental bristle holder 11 is mounted on the brush member 3, i.e. on the disc portion 6 of the brush member 3, so as to be movable, i.e. so as to be pivotable. The interdental bristle holder 11 can be driven by drive means, not shown, and performs a pivotable movement along a circular path when it is driven. Thus, it is achieved that the interdental bristle holder 11 performs a movement which is oriented substantially in the longitudinal direction of the interdental spaces between the teeth of a user.

The interdental bristle holder 11 has a further holder surface 12. In the area of the further holder surface 12 interdental bristles 13 project from the interdental bristle holder 11 transversely to the further holder surface 12, in the present case perpendicularly to the further holder surface 12. The interdental bristles 13 together form an interdental bristle field 14.

In the toothbrush 1 shown in FIGS. 1, 2 and 3 the bristle field 10 of the bristle holder 7 advantageously comprises a first field portion 15 and a second field portion 16. The first field portion 15 is situated at the side of the bristle holder 7 which faces the interdental bristle field 14 and the second field portion 16 is situated at the side of the bristle holder 7 which is remote from the interdental bristle field 14. Furthermore, in preferred embodiment the bristles 17 in the first field portion 15 are shorter than the interdental bristles 13 and the bristles 18 in the second field portion 16 are longer than the bristles 17 in the first field portion 15. Thus, the bristles 18 in the second field portion 16 at the same time form interdental bristles.

As is apparent from FIG. 2, all the bristles 17 in the first field portion 15 have the same length.

As is also apparent from FIG. 2, the free ends of the bristles 18 in the second field portion 16 are bounded by two bounding planes 19 and 20 which are inclined relative to one another and which are shown diagrammatically as dash-dot lines in FIG. 2.

With respect to the interdental bristles 13 it is to be noted that the interdental bristles 13 are moderately inclined relative to the interdental bristle holder 11, namely in such a manner that two groups of interdental bristles 13 are inclined towards one another, the longitudinal directions of the interdental bristles 13 of the two groups each being oriented at an angle β with respect to a normal to the further holder surface 12, which angle is approximately 10°.

In the toothbrush 1 as shown in FIGS. 1 to 3 the bristles in the second field portion 16 are, in addition, also available for tooth cleaning purposes in the interdental spaces, which results in a substantial improvement of the plaque removal in the interdental spaces in comparison with known toothbrushes and known brush members for toothbrushes. In addition, the longer bristles 18 in the second field portion 16 in conjunction with the longer interdental bristles 13 provide a correct positioning of the entire bristle configuration of the brush member 3 with respect to a tooth to be cleaned, which is advantageous for a proper tooth cleaning action both in the area of their lateral surfaces and in the area of the interdental spaces.

With regard to the bristle configuration of the toothbrush as shown in FIGS. 1, 2 and 3 it is to be noted that in a preferred embodiment the following length dimensions were selected for the individual bristle areas. The bristles 17 in the first field portion 15 were given a length of 7.6 mm. For the bristles 18 in the second field portion 16 a maximum length of 9.3 mm was selected. For the interdental bristles 13 a length of 11.0 mm was selected. Moreover, toothbrushes were tested in which the bristles 18 of the second field portion 16 had an equal length of approximately 9.5 to 10.0 mm.

The invention is not limited to the embodiment described hereinbefore by way of example. In a toothbrush in accordance with the invention the interdental bristle holder may alternatively be arranged adjacent a bristle holder at the side of this bristle holder nearest the grip member of a toothbrush, in which case the second field portion of the bristle field is disposed on the bristle holder at the side of the bristle holder remote from the grip member.

What is claimed is:

1. A toothbrush comprising a grip member and a brush member connected to the grip member, said brush member having a longitudinal axis and at its end remote from the grip member carrying a bristle holder which is drivable for pivotable movement between multiple positions through a center position along a circular path, said bristle holder being mounted on the brush member so as to be movable with respect to a holder axis and having a holder surface which extends substantially transversely to the holder axis and from which, in the area of the holder surface, bristles project transversely to the holder surface, said bristles together forming a first bristle field, and said brush member in addition comprising an interdental bristle holder, which is drivable for pivotable movement through a center position along a circular path and is disposed adjacent the bristle holder in the direction of the longitudinal axis of the brush member, said interdental bristle holder being mounted on the brush member so as to be movable and having a further holder surface and from which in the area of the further holder surface interdental bristles project transversely to the further holder surface, said interdental bristles together forming an interdental bristle field, wherein:

the first bristle field comprises a first field portion and a second field portion, the first field portion is disposed at the side of the bristle holder nearest the interdental bristle field and the second field portion is disposed at the side of the bristle holder remote from the interdental bristle field all the bristles of the first field portion are shorter than all the interdental bristles, all the bristles of the second field portion are longer than all the bristles of the first field portion and the bristles of the second field portion form interdental bristles.

2. A brush member for a toothbrush which brush member is adapted to be coupled detachably to a grip member of the toothbrush, said brush member having a longitudinal axis and at its end remote from the grip member carrying a bristle holder which is drivable for pivotable movement through a center position along a circular path, said bristle holder is mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, said bristles together forming a first bristle field, and in addition said brush member comprising an interdental bristle holder, which is drivable for pivotable movement through a center position along a circular path and is disposed adjacent the bristle holder in the direction of the longitudinal axis of the brush member, said interdental bristle holder is mounted on the brush member so as to be movable and having a further holder surface from which in the area of the further holder surface interdental bristles project transversely to the further holder surface, which interdental bristles together form an interdental bristle field, wherein:

the bristle field comprises a first field portion and a second field portion;

the first field portion is disposed at the side of the bristle holder nearest the interdental bristle field and the second field portion is disposed at the side of the bristle holder remote from the interdental bristle field, and the bristles of the first field portion are shorter than the interdental bristles, the bristles of the second field portion are longer than the bristles of the first field portion and the bristles of the second field portion form interdental bristles.

3. A toothbrush comprising a grip member and a brush member connected to the grip member, said brush member having a longitudinal axis and at its end remote from the grip member carrying a bristle holder which is drivable for pivotable movement through a center position along a circular path, said bristle holder being mounted on the brush member so as to be movable with respect to a holder axis which extends transversely to the longitudinal axis and having a holder surface which extends substantially transversely to the holder axis and from which, in the area of the holder surface, bristles project transversely to the holder surface, said bristles together forming a first bristle field, and in addition said brush member comprising an interdental bristle holder, which is drivable for pivotable movement through a center position and is disposed adjacent the bristle holder in the direction of the longitudinal axis of the brush member, said interdental bristle holder being mounted on the brush member so as to be movable and having a further holder surface and from which in the area of the further holder surface interdental bristles project transversely to the further holder surface, said interdental bristles together forming an interdental bristle field, wherein:

the first bristle field comprises a first field portion and a second field portion, the first field portion is disposed at the side of the bristle holder nearest the interdental bristle field and the second field portion is disposed at the side of the bristle holder remote from the interdental bristle field, all of the bristles of the first field portion have the same length and are shorter than all of the interdental bristles, and all of the bristles of the second field portion are longer than all of the bristles of the first field portion and the bristles of the second field portion form interdental bristles.

4. A toothbrush comprising a grip member and a brush member connected to the grip member, said brush member having a longitudinal axis and at its end remote from the grip member carrying a bristle holder which is drivable for pivotable movement along a circular path through a center position, said bristle holder being mounted on the brush member so as to be movable with respect to a holder axis which extents transversely to the longitudinal axis and having a holder surface which extends substantially transversely to the holder axis and from which, in the area of the holder surface, bristles project transversely to the holder surface, said bristles together forming a first bristle field, and said brush member in addition comprising an interdental bristle holder, which is drivable for pivotable movement through a center position along a circular path and is disposed adjacent the bristle holder in the direction of the longitudinal axis of the brush member, said interdental bristle holder being mounted on the brush member so as to be movable and having a further holder surface and from which in the area of the further holder surface interdental bristles project transversely to the further holder surface, said interdental bristles together forming an interdental bristle field, wherein:
- the first bristle field comprises a first field portion and a second field portion,
- the first field portion is disposed at the side of the bristle holder nearest the interdental bristle field and the second field portion is disposed at the side of the bristle holder remote from the interdental bristle field,
- all of the bristles of the first field portion are shorter than all of the interdental bristles,
- all of the bristles of the second field portion are longer than all of the bristles of the first field portion, the bristles of the second field portion form interdental bristles, and
- the bristles of the second field portion are bounded at their free ends by two bounding planes which are inclined with respect to one another in a wedge-like fashion.

5. A brush member for a toothbrush which brush member is adapted to be coupled detachably to a grip member of the toothbrush, said brush member having a longitudinal axis and at its end remote from the grip member carrying a bristle holder which is drivable for pivotable movement through a center position along a circular path, said bristle holder being mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, said bristles together forming a first bristle field, and said brush member in addition comprising an interdental bristle holder, which is drivable for pivotable movement through a center position along a circular path and is disposed adjacent the bristle holder in the direction of the longitudinal axis of the brush member, said interdental bristle holder being mounted on the brush member so as to be movable and having a further holder surface from which in the area of the further holder surface interdental bristles project transversely to the further holder surface, which interdental bristles together form an interdental bristle field, wherein:
- the first bristle field comprises a first field portion and a second field portion,
- the first field portion is disposed at the sides of the bristle holder nearest the interdental bristle field and the second field portion is disposed at the side of the bristle holder remote from the Interdental bristle field,
- all of the bristles of the first field portion all have the same length and are shorter than all of the interdental bristles,
- all of the bristles of the second field portion are longer than all of the bristles of the first field portion and the bristles of the second field portion Form interdental bristles.

6. A brush member as claimed in claim 5, wherein the bristles of the second field portion are bounded at their free ends by two bounding planes which are inclined with respect to one another in a wedge-like fashion.

* * * * *